US012805825B2

United States Patent
Becker et al.

(10) Patent No.: US 12,805,825 B2
(45) Date of Patent: Nov. 24, 2026

(54) DISTRIBUTED NETWORKED MEDICAL DEVICES

(71) Applicant: CARESTREAM HEALTH, INC., Rochester, NY (US)

(72) Inventors: Stephen Becker, Rochester, NY (US); Luca Bogoni, Philadelphia, PA (US); Frank A. West, Marion, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 125 days.

(21) Appl. No.: 18/995,954

(22) PCT Filed: Sep. 20, 2023

(86) PCT No.: PCT/US2023/074625
§ 371 (c)(1),
(2) Date: Jan. 17, 2025

(87) PCT Pub. No.: WO2024/064710
PCT Pub. Date: Mar. 28, 2024

(65) Prior Publication Data

US 2026/0033797 A1 Feb. 5, 2026

Related U.S. Application Data

(60) Provisional application No. 63/408,494, filed on Sep. 21, 2022.

(51) Int. Cl.
*A61B 6/00* (2024.01)

(52) U.S. Cl.
CPC .............. *A61B 6/563* (2013.01); *A61B 6/566* (2013.01); *A61B 6/4405* (2013.01)

(58) Field of Classification Search
None
See application file for complete search history.

(56) References Cited

U.S. PATENT DOCUMENTS

2014/0180702 A1 6/2014 Mansker et al.
2014/0275954 A1 9/2014 Ohta et al.
(Continued)

OTHER PUBLICATIONS

International Search Report mailed on Jan. 2, 2024 for International Application No. PCT/US2023/074625, 3 Pages.

*Primary Examiner* — Marcus H Taningco
(74) *Attorney, Agent, or Firm* — Eugene I Shkurko

(57) ABSTRACT

A distributed radiographic imaging system is formed using a radiographic imaging apparatus having a radiographic energy source and a digital radiographic detector, a first computer system, and a second computer system. The components of the distributed imaging system are communicatively connected. The radiographic imaging apparatus and the first computer system wirelessly communicate when they are in a predefined proximity with each other. The second computer system determines if the radiographic imaging apparatus is currently being used in an exclusive imaging session and, in response to an exclusive session request, transmits a session approval token to the first computer system and to the radiographic imaging apparatus if the radiographic imaging apparatus is not currently being used in an exclusive imaging session. The first computer system and the radiographic imaging apparatus establish an exclusive communication and control session in response to receiving the session approval token.

15 Claims, 5 Drawing Sheets

(56) References Cited

U.S. PATENT DOCUMENTS

| | | | | |
|---|---|---|---|---|
| 2019/0005263 | A1* | 1/2019 | Holl | H04L 67/141 |
| 2019/0231297 | A1* | 8/2019 | Takekoshi | A61B 6/467 |

* cited by examiner

DISTRIBUTED NETWORKED MEDICAL DEVICES

CROSS REFERENCE TO RELATED APPLICATIONS

This application claims the benefit of and is a U.S. National Phase filing of PCT Application PCT/US2023/074625 filed Sep. 20, 2023 entitled "DISTRIBUTED NETWORKED MEDICAL DEVICES", in the name of Becker et al., which claims the benefit of U.S. Patent Application Ser. No. 63/408,494, filed Sep. 21, 2022, in the name of Becker et al., and entitled DISTRIBUTED NETWORKED MEDICAL DEVICES.

BACKGROUND OF THE INVENTION

The subject matter disclosed herein relates to medical device components that are associated over a network and cooperate to perform medical imaging.

Standard hardware and software architectures for medical devices, that enable the acquisition, operation and processing of acquired images, are mostly located proximally or on board of a single device. These devices tend to exhibit closed and static architectural design which require limited and costly procedures to upgrade. Furthermore, these architectures have additional drawbacks when considering development and testing, time to market, regulatory requirements and clearance, serviceability, deployment of product and cybersecurity upgrades.

For instance, a mobile digital radiography (DR) solution is typically designed as a self-contained movable cart that includes several components such as: a voltage generator, an x-ray source, motion control for wheels, communication (wired or wireless), connections to the DR detector and to the host network; hardware and software for image reconstruction as well as advanced image processing capabilities, storage, and usually a user interface having a means to visualize and validate the clinical quality of the acquired image(s). As more hardware and software are deployed in the field, the software for any feature must consider all products involved and their configurations.

The discussion above is merely provided for general background information and is not intended to be used as an aid in determining the scope of the claimed subject matter.

BRIEF DESCRIPTION OF THE INVENTION

A distributed radiographic imaging system is formed using a radiographic imaging apparatus having a radiographic energy source and a digital radiographic detector, a first computer system, and a second computer system. The components of the distributed imaging system are communicatively connected. The radiographic imaging apparatus and the first computer system wirelessly communicate when they are within a predefined proximity with each other. The second computer system determines if the radiographic imaging apparatus is currently being used in an exclusive imaging session and, in response to an exclusive session request, transmits a session approval token to the first computer system and to the radiographic imaging apparatus if the radiographic imaging apparatus is not currently being used in an exclusive imaging session. The first computer system and the radiographic imaging apparatus establish an exclusive communication and control session in response to receiving the session approval token In one embodiment, a distributed radiographic imaging system includes a radiographic imaging apparatus with an x-ray source and digital radiographic detector, a first computer system, and a second computer system communicatively connected. The radiographic imaging apparatus and the first computer system are configured to wirelessly communicate with each other and to recognize each other when the first computer system is in a predefined proximity to the radiographic imaging apparatus. The second computer system communicates with the radiographic imaging apparatus to determine if it is currently being used in an exclusive imaging session. The second computer system transmits a session approval token to the first computer system and to the radiographic imaging apparatus if it is not currently being used in an exclusive imaging session. The first computer system and the radiographic imaging apparatus establish an exclusive communication and control session in response to receiving the session approval token.

In another embodiment, a method of forming a distributed radiographic imaging system includes providing a radiographic imaging apparatus having an x-ray source and a digital radiographic detector. A first computer system, a second computer system, and the radiographic imaging apparatus are communicatively connected to each other. The radiographic imaging apparatus and the first computer system wirelessly communicate with each other and identify each other when the first computer system and the radiographic imaging apparatus are within a predefined proximity. The second computer system receives a request to approve an exclusive session as between the first computer system and the radiographic imaging apparatus. In response, the second computer system determines if the radiographic imaging apparatus is currently being used in an exclusive imaging session. The second computer system transmits the requested session approval token to the first computer system and to the radiographic imaging apparatus if it determines that the radiographic imaging apparatus is not being currently used in an exclusive imaging session. An exclusive communication and control session between the first computer system and the radiographic imaging apparatus is established in response to receiving the session approval token.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation., emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 63/408,494, filed Sep. 21, 2022, in the name of Becker et al., and entitled DISTRIBUTED NETWORKED MEDICAL DEVICES, which is hereby incorporated by reference herein in its entirety.

The present invention is directed to programmably associating constituent components of a medical device. In one embodiment, an activation and locking mechanism enables distributed components of the medical device to be operated as a unitary networked medical device. Just as a medical device may be decomposed into component parts, these parts may become activated as a unit upon being programmably locked into an active medical device configuration by sharing a temporary security key among the component parts. Issuing the security key to the component parts may be triggered by a signal, or token, transmitted to the shared components to be configured as such, which locks them into an active device configuration to perform a specific medical task. Once the components are locked, they may remain in an exclusive locked configuration for the duration of the clinical task. Upon the programmed release of the lock, the components may be deactivated, resume their previous status, and/or they may be reconfigured as part of another networked medical device.

Embodiments disclosed herein have no constraint that requires the device's components (hardware and software) to be co-located in or on the same physical platform. Embodiments disclosed herein expand the association of components, and communications between components, from being hard-wired or wireless within one physical device to a more flexible and larger network that affords a virtual and dynamic structure of component devices. A user interface is generalized so that user interaction for clinical acquisition, verification, validation, and service, such as device configuration, performance monitoring, and upgrades, may be performed on various platforms that include basic interfaces using web browsers. Additional features may include decoupling the upgradability of computational components, localizing the processing components on a server within the premises or on a private and/or public cloud, introducing a mechanism to dynamically and on-demand lock a set of components into a constituted active medical device.

Figure 2:
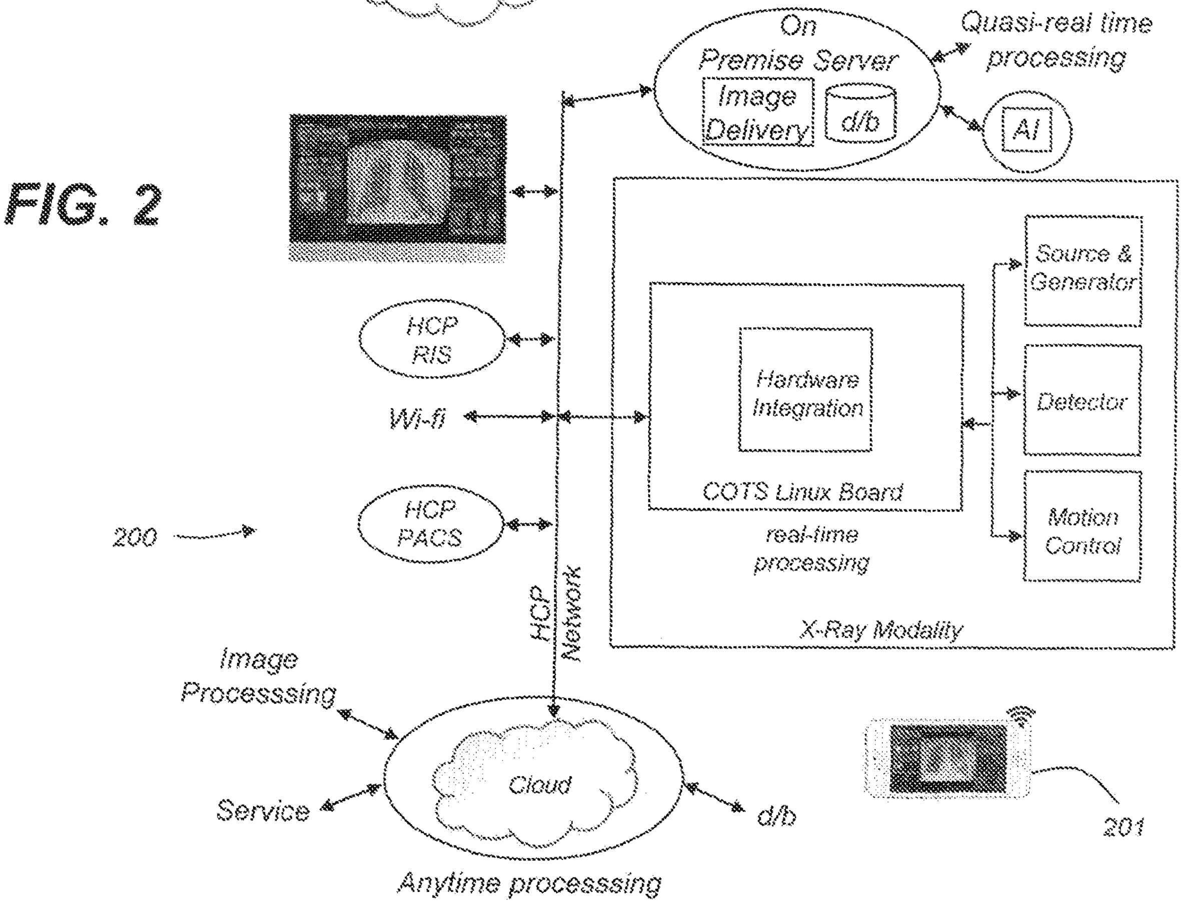
FIG. 2 is schematic diagram of an exemplary decentralized representation of a mobile digital radiography cart.

In one embodiment, a feature for triggering an active networked medical device may be based on a locking mechanism. A networked medical device may be formed using a portable computer device having a user interface, such as a laptop, mobile phone, iPad, tablet and the like, capable of generating a locking key. In a different embodiment, using the example of a mobile cart digital radiography (DR) system, the DR detector may be directly connected to the larger network and communicate with a centralized server. In other embodiments, the mobile cart may host one of x-ray, digital tomography, serial radiography, and fluoroscopy modalities. In one embodiment, the decentralization of services, as illustrated in FIG. 2, may reside within a Windows PC. The mobile DR system so embodied presents a distributed architecture based on timely computational responses to operations and interactions within the system.

The time terminology, as used herein, may be characterized as follows: real-time-requiring low latency response: ≤10 ms, as exemplified by interactions between source, generator and detector; quasi-real-time: ≤2 mins, exemplified by image reconstruction or specific image enhancement; and any-time: >2 mins, capturing processing that may impact clinical workflow, diagnostic decisions, and patient management.

Figure 1:
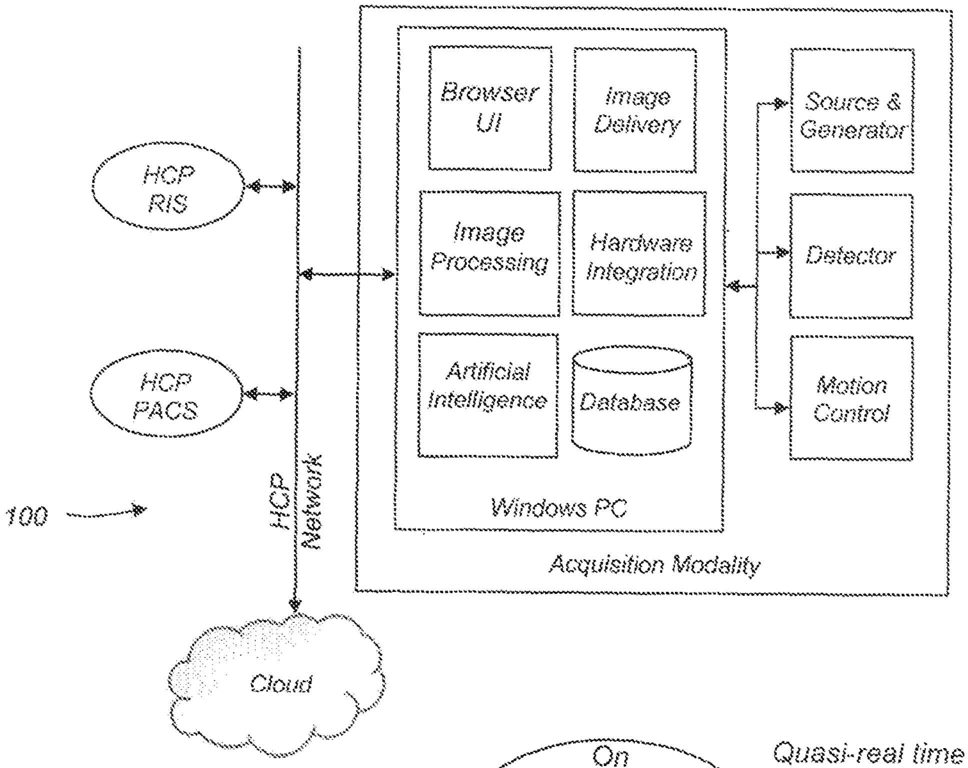
FIG. 1 is a schematic diagram of an exemplary generic architecture for an imaging device.

With reference to FIG. 1 and FIG. 2, a medical imaging device 100, 200, distributed over a network may be organized as a centralized or distributed architecture of the constituent components. A distributed medical imaging device structured with a centralized architecture may include any number of the following components; processing capabilities to perform data processing and/or reconstruction from raw image acquisitions; coordinating business logic to component sequencing and controls; data storage and retrieval; advanced data and image processing capabilities, which may be supported by specialized hardware; user interface to enable interactions with the medical device; implementation of specific clinical workflows, visualizations of acquired or processed data—such a UI may be hosted as a cloud service; one or more active sources, such as x-ray, including generator(s) and controls; one or more imaging detectors to enable image acquisition from active or passive sources; motion components and controls displacements of acquisition components relative to one another; a software-enabled key locking mechanism to activate a collection of network components, according to some preestablished configurations, into an operable medical device which may be used for specific clinical tasks; and communication infrastructure, wired or wireless, to support real-time, quasi-real-time and any-time processing. It should be understood that in the event the communication infrastructure can't support real-time communication, a specialized communication link may be applied to those components which have real-time requirements.

The locking mechanism described herein may implement unique digital identifiers associating resources, such as devices, personnel, clinical exam requirements, and a map overlay for displaying a visual worklist. Different associations and/or groupings of the components may be used, thereby introducing hierarchical relations between components. A non-centralized architecture of components may enable data to be shared between components in an independent manner to improve an acquisition or interaction opportunity in response to preliminary acquisition, such as image scouts or SID computation.

The present invention describes an architecture of device components and services of a medical device over a network instead of being integrated into only one or more physical devices. This architectural composition enables a multitude of distinct physical components to be digitally associated, statically or dynamically, to define a medical device network. Components may become a network instantiation of a medical device depending on components being registered, manually or automatically. This architecture allows a large variety of configurations to be tailored and refined to meet clinical needs. One fundamental aspect to convert networked components into an unitary active medical imaging device is the introduction of a shared locking capability which binds a group of components via communicating with a central server.

With reference to FIG. 1, image acquisition components (e.g., source, detector & controls) as well as imaging reconstruction & processing, UI interface, advanced image/sensors processing (AI) and storage are located on the device and communicate to the hosting health care (HCP) network via direct cable or wirelessly. Acquisition modalities range from DR room, a CT, to mobile DR or mobile carts. Decomposing the medical device architecture and relaxing standard architectural structures is achieved by: (1) transferring reconstruction and advanced image processing components, storage, UI from the device to one or more local servers; (2) communication not only within the health care local network but alternative subnetworks of 5G; (3) and further decoupling of the constituent devices;

With reference to FIG. 2, the capabilities that previously resided within the device itself as illustrated by the "Window PC" box in FIG. 1 have now been distributed over the network. This distribution exhibits user interfaces available at a standard console and/or on a phone and/or tablet, with Wi-Fi communication with the server performing the original functionality. The portable device 201, illustrated here as mobile phone, may trigger the locking mechanism so that all the components may be activated as a unitary networked medical device. Additionally, this figure illustrates augmented capabilities that may be directly available as a byproduct of decentralization. These are highlighted as connected to cloud-based solutions, such as image processing, services, and databases.

Figure 3:
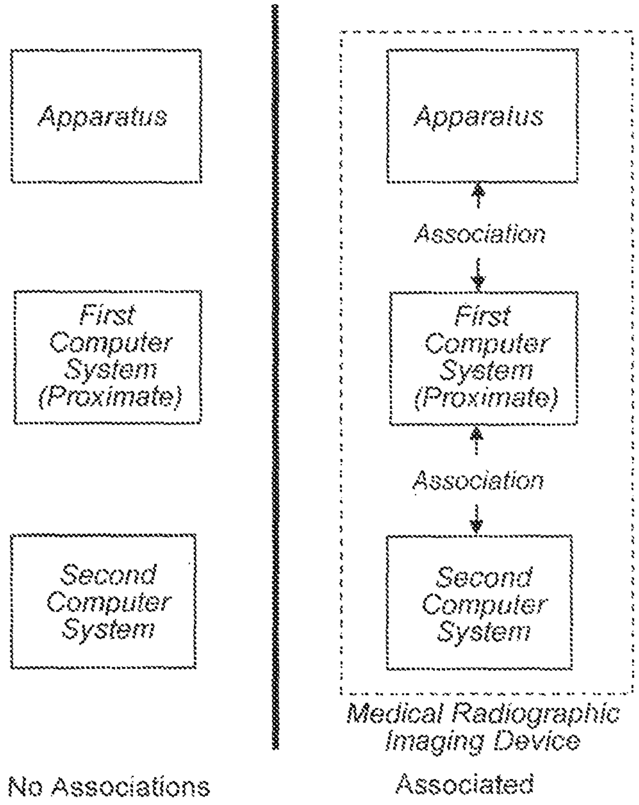
FIG. 3 is a schematic diagram of exemplary individual components which become a specific instance of a medical radiographic imaging device when associated.

With reference to FIG. 3, left side, there is illustrated a schematic diagram of exemplary individual components which become a specific instance of a networked medical radiographic imaging device when they are associated. The components may include a medical apparatus of any type, a first computer system, which may be portable, and a second computer system, as described herein. A distributed medical radiographic imaging device may be formed, FIG. 3, right side, when the components are associated, as described herein.

Figure 4:
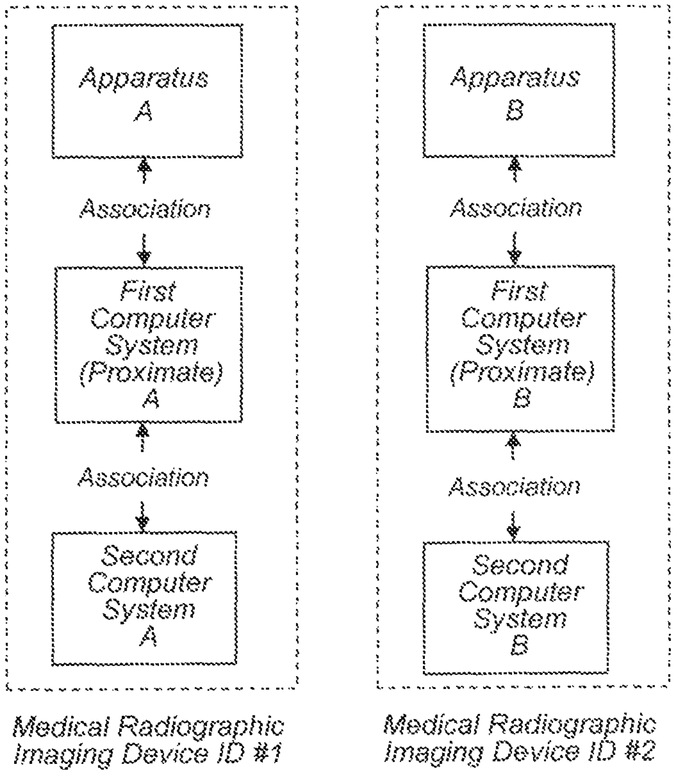
FIG. 4 is a diagram of an exemplary set of components associated as two separate medical radiographic imaging devices.

With reference to FIG. 4, left side, components labeled A may be associated to create a networked medical device #1. In FIG. 4, right side, components labeled B may be associated to create a medical device #2. The components may include medical apparatuses of any type, first computer systems, which may be portable, and second computer systems, as described herein.

Figure 5:
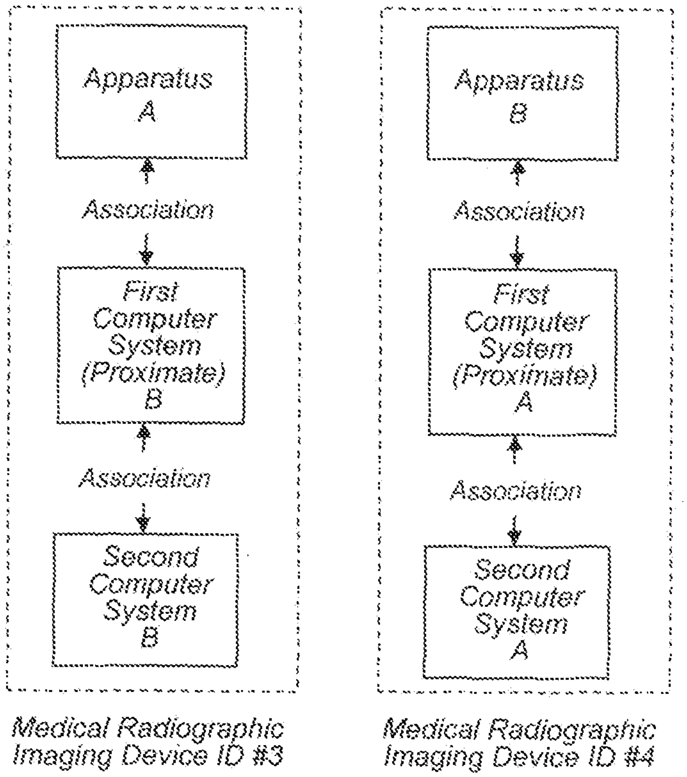
FIG. 5 is a diagram of an exemplary alternate combination of associated components A and B to create devices #3 and #4.

With reference to FIG. 5, there is illustrated various potential alternate combinations of associated components labeled A and B, as described herein, to create devices #3 and #4. These exemplary configurations illustrate that the associations as between components may be interchangeable, fluid and transitory. Namely, components that constitute an activated networked medical device by associating apparatus A, a first computer A, and a second computer A, as in FIG. 4, may be interchangeably embodied with apparatus A, a first computer B and a second computer B to form medical device #3. Similarly, an activated networked medical device may be formed by associating apparatus B, a first computer A, and a second computer A to form device #4.

Figure 6:
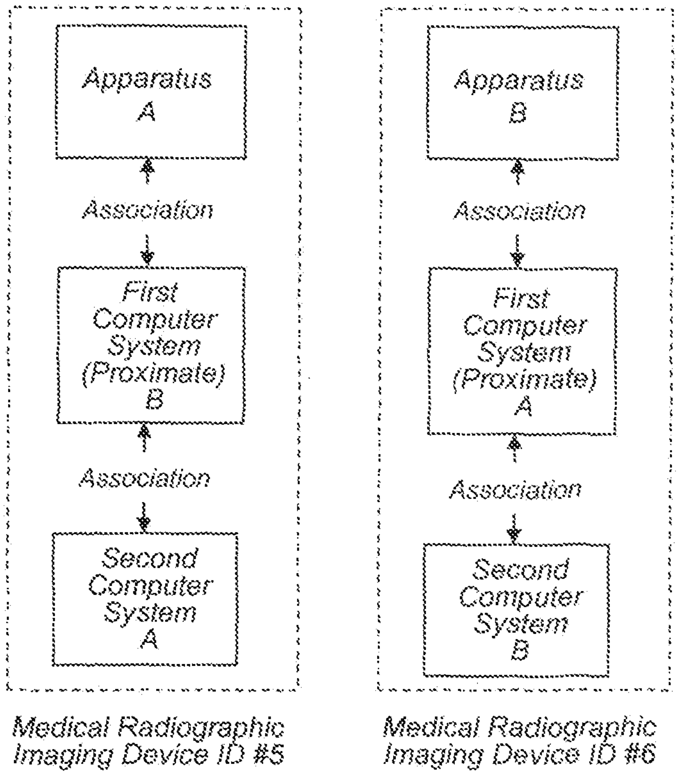
FIG. 6 is a diagram of an exemplary alternate combination of associated components A and B to create devices #5 and #6.

With reference to FIG. 6, there is illustrated further exemplary alternate combinations of associated components labeled A and B to create devices #5 and #6. As illustrated, networked medical imaging devices may be interchangeably created by using or swapping a first computer between two instances of the medical devices as illustrated.

Figure 7:
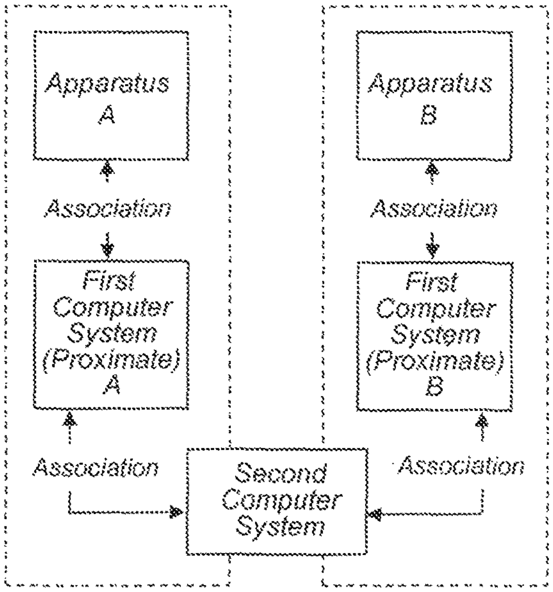
FIG. 7 is a diagram of an exemplary alternate association of components A and B with a shared second computer system.

With reference to FIG. 7, there is illustrated a diagram of an exemplary alternate association of components A and B with a shared second computer system, such as an application server. Both medical radiographic imaging devices, with components labeled A and B, are unique instances, but the second computer system, such as an application server, can be shared.

Figure 8:
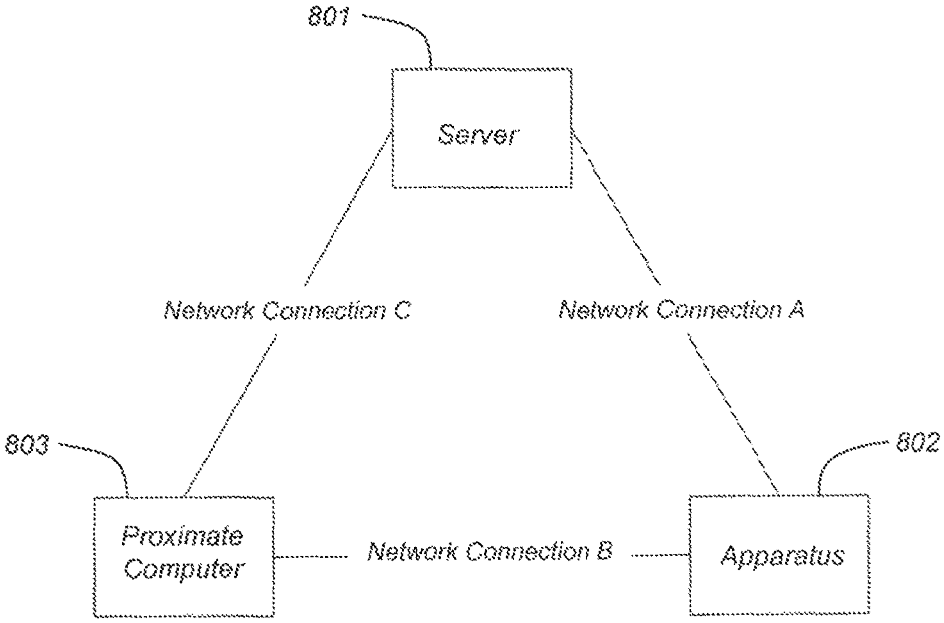
FIG. 8 is schematic network diagram of an example embodiment of a distributed networked medical device.

With reference to FIG. 8, a server 801 is connected over network connection A to a medical apparatus 802; the medical apparatus 802 is connected over network connection B to a user computer 803; and the server 801 is connected over network connection C to the user computer 803. The server 801 may include software applications as described herein; the medical apparatus 802 may be a physical device for medical use; and the user computer 803 may be a computer in local proximity of the medical apparatus 802 to provide a user interface (UI) for controlling the medical apparatus 802. The network connections A, B, C, each provide a digital wired or wireless communication path between the devices shown. If any one of the network connections A, B, C, is omitted, digital communication between any two devices as shown may still be performed using the the other two network connections either directly or indirectly.

Figure 9:
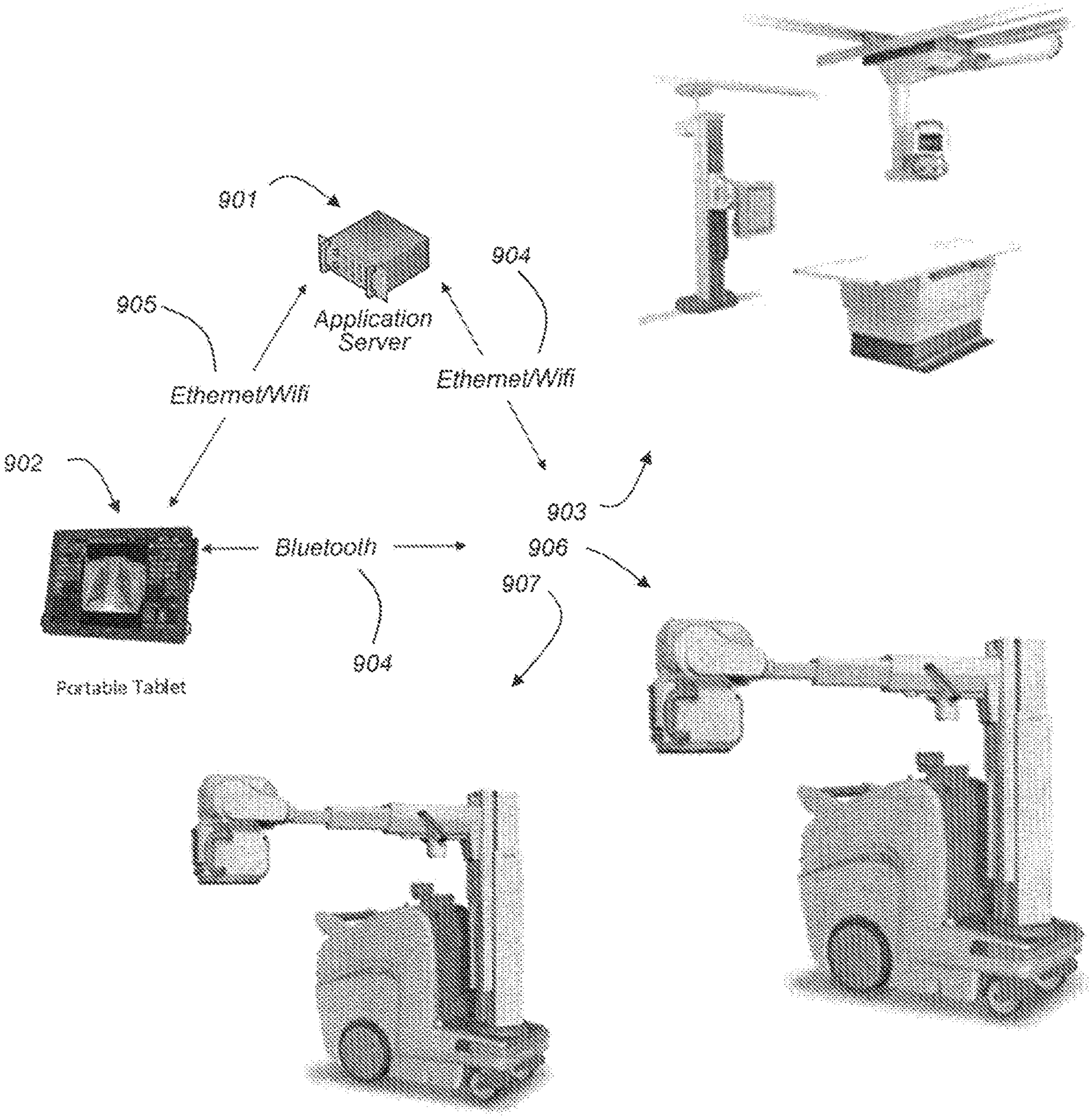
FIG. 9 is a schematic network diagram of example embodiments of x-ray imaging apparatuses and a portable tablet using manual or automatic association.

In one particular embodiment, and with reference to FIG. 9, an application server 901, a portable tablet computer 902, providing a user interface and device control software, and an x-ray imaging system 903, define an example component set that may be associated, as described herein, to form a unitary networked medical device. Network connection 904, for example Ethernet or Wi-Fi, is a communication path between application server 901 and x-ray imaging system 903; network connection 904 is a communication path, for example Bluetooth, between the tablet computer 902 and the x-ray imaging system 903; and network connection 905 is a communication path, for example Ethernet or Wi-Fi between the application server 901 and the tablet computer 902. Any one of the network connections may be omitted, whereby communication between any two components can be performed through the existing two network connections, directly or indirectly. As depicted in FIG. 9, the imaging system 903 may include an x-ray imaging system for use in an examination room having a wall and/or table mounted DR detector and a ceiling mounted tube crane for controlling movement of a tube head, each of which may be controlled by a user via the UI of the tablet computer 902. While a tablet computer 902 is depicted as providing a UI for the user, alternative user devices may include a mobile phone or a tethered workstation PC. The user computer 802, 902, may be shared among multiple apparatuses. The server 801, 901, may be located, for example, in a hospital data center or it may be more remotely located from the x-ray imaging system 903. The server 801, 901, may be shared among one or more apparatuses 803, 903, and one or more computers 802, 902.

A certificate created by server 901 may be installed on imaging system 903 via a standard provisioning process used as a trust certificate for the x-ray imaging system 903. A server created certificate may be similarly installed on the tablet computer 902. In one example embodiment, a user may approach the x-ray imaging system 903, for example at a distance of about thirty (30) feet or less, carrying the tablet computer 902, which may be configured to communicate wirelessly over the connected communication networks 904, 905. The user may then input into the tablet computer 902 a unique ID code assigned to the x-ray imaging system 903 via QR code scan or manually. The tablet computer 902 then communicates to application server 901 and requests an exclusive session for the x-ray imaging system 903 identified via the unique code. The application server 901 verifies the code of the x-ray imaging system 903 and checks that it is not currently in an exclusive session. If the x-ray imaging system 903 is not currently associated with a session, the application server 901 will generate a session token and send it to the x-ray imaging system 903 and to the tablet computer 902. The tablet computer 902 then wirelessly connects to the x-ray imaging system 903, for example via a Bluetooth connection, and exchanges a session token via a remote procedure call channel (gRPC). After the x-ray imaging system 903 accepts the session token it locks itself into an exclusive session with the tablet computer 902. The active networked medical device now consists of an exclusive, three-way, encrypted session between the application server 901, the tablet computer 902, and the x-ray imaging system 903. The user may now perform x-ray imaging via UI software controls on the tablet computer 902 and/or hardware controls on the imaging device itself. Acquired radiographic image data may be passed from the x-ray imaging system 903 to both the tablet computer 902 and to the application server 901. Application functions may be communicated between the tablet computer 902 and the application server 901. Upon completion of an imaging session, the user may terminate the session using the UI which sends a message to the application server 901 which then informs the x-ray imaging system 903 that the session is terminated, after which the Bluetooth network connection is dropped by either the tablet computer 902 and/or the x-ray imaging system 903, thereby unlocking the x-ray imaging system 903. If at any time during the locked session the network connections to the server are dropped, the exclusive session will not be terminated. This allows the user to continue operating the x-ray imaging system 903 in the event of a server outage, although functionality may be limited.

Continuing with reference to FIG. 9, the medical apparatus 802 used to form a unitary networked medical device, as described above, may include a portable bedside fluoroscopy system 906, as an alternative to the x-ray imaging system 903, and the application server 901 may include a server computer located in a cloud data center, as described in relation to FIG. 2. This application server 901 may be shared among one or more apparatuses 802, 903, 906, and one or more user computers 802, 902. As described above, a server created trust certificate is provided to the imaging device—the portable bedside fluoroscopy system 906, and to the user's tablet computer 902.

In one example embodiment, a user may approach the portable bedside fluoroscopy system 906 carrying the tablet computer 902, for example, at a distance of about thirty (30) feet or less, which may be configured to communicate wirelessly over the connected communication networks 904, 905. The portable bedside fluoroscopy system 906 may detect the wireless tablet computer 902 and, in response, wirelessly transmits a request for the tablet computer's certificate information. The portable bedside fluoroscopy system 906 receives the tablet's certificate information and shares it with the application server 901 to verify that the tablet computer 902 is trusted. If trusted, the network connection 904 is allowed to continue; if not trusted, the network connection is dropped. If trusted, the tablet computer 902 communicates to application server 901 and requests an exclusive session for the portable bedside fluoroscopy system 906. The application server verifies the identity of the portable bedside fluoroscopy system 906 and checks that it is not currently in an exclusive session. The application server 901 generates a session token and sends it to the portable bedside fluoroscopy system 906 and to the tablet computer 902. The tablet computer 902 connects to the portable bedside fluoroscopy system 906 via Bluetooth and exchanges a session token via a gRPC channel. The portable bedside fluoroscopy system 906 accepts the session token and locks itself for an exclusive session with the tablet computer 902. The networked medical device now consists of an exclusive, three-way, encrypted session between the application server 901, the tablet computer 902, and the portable bedside fluoroscopy system 906. The user may perform bedside fluoroscopic imaging via UI software controls on the tablet computer 902 and/or hardware controls on the portable bedside fluoroscopy system 906 itself. Image data acquired by the portable bedside fluoroscopy system 906 may be transmitted to both the tablet computer 902 and to the application server 901. Application functions may be communicated between the application server 901 and the tablet computer 902. Upon completing fluoroscopic imaging, the user may terminate the session via the UI or by walking away, carrying the tablet computer 902 until it is no longer proximate to the portable bedside fluoroscopy system 906. The Bluetooth connection is then dropped, the session is terminated, and the portable bedside fluoroscopy system 906 is unlocked for the next operator. The user may then approach another medical apparatus with the same tablet computer 902 and repeat the procedure to establish an exclusive session with a different medical apparatus seamlessly. If at any time during the locked session the Ethernet network connections to the server are dropped, the exclusive session will not be terminated. This allows the user to continue operating the portable bedside fluoroscopy system 906 in the event of a server outage, although functionality may be limited.

In the case of the portable bedside fluoroscopy system 906 example described above, while there may be various embodiments of communication configurations, in practice there may be additional accessories included in the network, such as a monitor connected via Ethernet/Wi-Fi to the application server 901 to enable visualization of streaming x-ray images. Hence, whereas the tablet computer 902, once connected, can be used to configure the image acquisition characteristics, visualization of streaming x-ray images may be performed on an accessory monitor.

Continuing with reference to FIG. 9, the medical device used to form a unitary networked medical device, as described above, may include a portable serial radiography device 907, as an alternative to the x-ray imaging system 903 and the portable bedside fluoroscopy system 906. The application server 901 may include a server computer located in a cloud data center, as described in relation to FIG. 2. This application server 901 may be shared among one or more apparatuses 802, 903, 906, 907, and one or more user computers 802, 902. As described above, a server created trust certificate is provided to the imaging device—the portable serial radiography device 907, and to the user's tablet computer 902.

In one example embodiment, a user may approach the portable serial radiography device 907 carrying the tablet computer 902, which may be configured to communicate wirelessly over the connected communication networks 904, 905. The portable serial radiography device 907 may detect the wireless tablet computer 902 and, in response, wirelessly transmits a request for the tablet computer's certificate information. The portable serial radiography device 907 receives the tablet's certificate information and shares it with the application server 901 to verify that the tablet computer 902 is trusted. If trusted, the network connection 904 is allowed to continue; if not trusted, the network connection is dropped. If trusted, the tablet computer 902 communicates to application server 901 and requests an exclusive session for the portable serial radiography device 907. The application server 901 verifies the identity of the portable serial radiography device 907 and checks that it is not currently in an exclusive session. If the portable serial radiography device 907 is not in an exclusive session, the application server 901 generates a session token and sends it to the portable bedside fluoroscopy system 906 and to the tablet computer 902. The tablet computer 902 connects to the portable serial radiography device 907 via Bluetooth and exchanges the session token via a gRPC channel. The portable serial radiography device 907 accepts the session token and locks itself for an exclusive session with the tablet computer 902. The newly formed networked medical device now consists of an exclusive, three-way, encrypted session between the application server 901, the tablet computer 902, and the portable serial radiography device 907. The user may perform bedside serial radiographic imaging via UI software controls on the tablet computer 902 and/or hardware controls on the portable serial radiography device 907 itself. Image data acquired by the portable serial radiography device 907 may be transmitted to both the tablet computer 902 and to the application server 901. Application functions may be communicated between the application server 901 and the tablet computer 902. Upon completing serial radiographic imaging, the user may terminate the session via the UI or by walking away, carrying the tablet computer 902 until it is no longer proximate to the portable serial radiography device 907. The Bluetooth connection is then dropped, the exclusive session is terminated, and the portable serial radiography device 907 is unlocked for the next operator. The user may then approach another medical apparatus with the same tablet computer 902 and repeat the procedure to establish an exclusive session with a different medical apparatus seamlessly. If at any time during the locked session the Ethernet network connections to the server are dropped, the exclusive session will not be terminated. This allows the user to continue operating the portable serial radiography device 907 in the event of a server outage, although functionality may be limited.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, C++or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A distributed radiographic imaging system comprising:

a radiographic imaging apparatus including a radiographic energy source and a digital radiographic detector;

a first computer system; and a second computer system communicatively connected to the first computer system, wherein the radiographic imaging apparatus and the first computer system are configured to wirelessly communicate with each other and to recognize each other when the first computer system is in a predefined proximity to the radiographic imaging apparatus, the second computer system is configured to communicate with both the first computer system and the radiographic imaging apparatus, to determine if the radiographic imaging apparatus is currently being used in an exclusive imaging session, and to transmit a session approval token to the first computer system and to the radiographic imaging apparatus if the radiographic imaging apparatus is not currently being used in an exclusive imaging session, and wherein the first computer system and the radiographic imaging apparatus establish a first exclusive communication and control session in response to receiving the session approval token.

2. The system of claim 1, wherein the first exclusive communication and control session is configured to enable the first computer system to control operation of the radiographic imaging apparatus, list radiographic imaging apparatus exam requests, to control radiographic image acquisition, processing, visualization, quality assessment, and external delivery of acquired radiographic images.

3. The system of claim 1, wherein communications between the first and second computer systems are performed through a wireless or wired connection, Wi-Fi, Bluetooth, near filed communication (NFC), infrared (IR) or a physical tethered connection.

4. The system of claim 1, further comprising:

a second radiographic imaging apparatus including a second radiographic energy source and a second digital radiographic detector;

a third computer system; and the second computer system communicatively connected to the third computer system, wherein the second radiographic imaging apparatus and the third computer system are configured to wirelessly communicate with each other and to recognize each other when the third computer system is in a predefined proximity to the second radiographic imaging apparatus, the second computer system is configured to communicate with both the third computer system and the second radiographic imaging apparatus, and to transmit a second session approval token to third computer system and the second radiographic imaging apparatus, and wherein the third computer system and the second radiographic imaging apparatus establish a second exclusive communication and control session, simultaneously with the first exclusive communication and control session, in response to receiving the second session approval token.

5. The system of claim 4, wherein the first and second radiographic imaging apparatuses are selected from a portable, mobile, or fixed radiographic imaging system, including general radiography and fluoroscopic imaging.

6. The system of claim 1, wherein the first computer system is configured to establish a proximity interlock with the radiographic imaging apparatus so that the first exclusive communication and control session is released if the first computer system moves out of the predefined proximity.

7. The system of claim 1, wherein the first computer system is configured to detect a location of the radiographic imaging apparatus and to digitally access an acquisition study protocol and a patient name based on the detected location of the radiographic imaging apparatus.

8. The system of claim 7, wherein the first computer system comprises a monitor and is configured to display the detected location on the monitor using a map overlay.

9. A method of forming a distributed radiographic imaging system, the method comprising:

providing a radiographic imaging apparatus including a radiographic energy source and a digital radiographic detector;

communicatively connecting a first computer system, a second computer system, and the radiographic imaging apparatus;

the radiographic imaging apparatus and the first computer system wirelessly communicating with each other and identifying each other when the first computer system and the radiographic imaging apparatus are within a predefined proximity to each other;

the second computer system receiving a request to approve an exclusive session as between the first computer system and the radiographic imaging apparatus;

the second computer system determining if the radiographic imaging apparatus is currently being used in an exclusive imaging session;

the second computer system transmitting a first session approval token to the first computer system and to the radiographic imaging apparatus in response to the second computer system determining that the radiographic imaging apparatus is not currently used in an exclusive imaging session; and establishing a first exclusive communication and control session between the first computer system and the radiographic imaging apparatus in response to receiving the first session approval token.

10. The method of claim 9, further comprising enabling the first computer system to control operation of the radiographic imaging apparatus, to list radiographic imaging apparatus exam requests, to control radiographic image acquisition, processing, visualization, quality assessment, and external delivery of acquired radiographic images in response to establishing the first exclusive communication and control session.

11. The method of claim 9, further comprising using any one or more of a wireless or wired connection, Wi-Fi, Bluetooth, near filed communication (NFC), infrared (IR) or a physical tethered connection between the first and second computer systems.

12. The method of claim 9, further comprising:

providing a second radiographic imaging apparatus including a second radiographic energy source and a second digital radiographic detector;

communicatively connecting the second computer system, a third computer system, and a second radiographic imaging apparatus;

the second radiographic imaging apparatus and the third computer system wirelessly communicating with each other and identifying each other when the third computer system and the second radiographic imaging apparatus are within a predefined proximity to each other;

the second computer system receiving a request to approve a second exclusive session as between the third computer system and the second radiographic imaging apparatus;

the second computer system determining if the second radiographic imaging apparatus is currently being used in an exclusive imaging session;

the second computer system transmitting a second session approval token to the third computer system and to the second radiographic imaging apparatus in response to the second computer system determining that the second radiographic imaging apparatus is not currently used in an exclusive imaging session; and establishing a second exclusive communication and control session, simultaneously with the first exclusive communication and control session, between the third computer system and the second radiographic imaging apparatus in response to receiving the second session approval token.

13. The method of claim 12, further comprising selecting the first and second radiographic imaging apparatuses from a portable, mobile, or fixed radiographic imaging system, including general radiography and fluoroscopic imaging.

14. The method of claim 9, further comprising establishing a proximity interlock so that the first exclusive communication and control session is released if the first computer system and the radiographic imaging apparatus are no longer within the predefined proximity.

15. The method of claim 9, further comprising digitally accessing an acquisition study protocol and a patient name based on a detected location of the radiographic imaging apparatus.

* * * * *